United States Patent [19]

Hon et al.

[11] Patent Number: 5,070,888
[45] Date of Patent: Dec. 10, 1991

[54] EXTERNAL UTERINE CONTRACTION MONITORING DEVICE

[75] Inventors: Edward H. Hon; Edward D. Hon, Both of Bradbury; Robert W. Hon, Los Altos, all of Calif.

[73] Assignee: The Hon Group, Encino, Calif.

[21] Appl. No.: 915,130

[22] Filed: Oct. 2, 1986

Related U.S. Application Data

[63] Continuation-in-part of Ser. No. 780,398, Sep. 26, 1985, and a continuation-in-part of Ser. No. 858,713, May 2, 1986.

[51] Int. Cl.$^5$ .............................................. A61B 5/103
[52] U.S. Cl. ..................................... 128/778; 128/775
[58] Field of Search ............................... 128/774–775, 128/778, 780, 782, 687, 639–640, 715, 802–803, 798, 662.04

[56] References Cited

U.S. PATENT DOCUMENTS

| | | | |
|---|---|---|---|
| 749,854 | 1/1904 | Fahrney | 128/687 X |
| 3,299,882 | 1/1967 | Masino | 128/687 X |
| 3,520,294 | 7/1970 | Fuzzell et al. | 128/775 |
| 3,795,241 | 3/1974 | Golovko | 128/640 |
| 3,824,988 | 7/1974 | Soldner et al. | 128/662.04 |
| 3,913,563 | 10/1975 | Ball | 128/775 |
| 3,945,373 | 3/1976 | Tweed et al. | 128/782 |
| 4,122,837 | 10/1978 | Leonard | 128/774 |
| 4,159,640 | 7/1979 | Leveque et al. | 128/774 X |
| 4,240,444 | 12/1980 | Virgulto et al. | 128/782 |
| 4,355,643 | 10/1982 | Laughlin et al. | 128/662.04 |
| 4,367,755 | 1/1983 | Bailey | 128/802 X |
| 4,537,197 | 8/1985 | Hulka | 128/361 X |
| 4,583,551 | 4/1986 | Pike | 128/640 |
| 4,640,295 | 2/1987 | Isaacson | 128/775 X |
| 4,657,022 | 4/1987 | Holscher | 128/640 X |

Primary Examiner—Angela D. Sykes
Attorney, Agent, or Firm—Lewis Anten

[57] ABSTRACT

An improved monitoring device for externally monitoring labor contractions preceding childbirth which does not require the use of a belt is disclosed consisting of a transducer assembly removably fixed to a base adhesively attached to the abdomen of the woman.

65 Claims, 6 Drawing Sheets

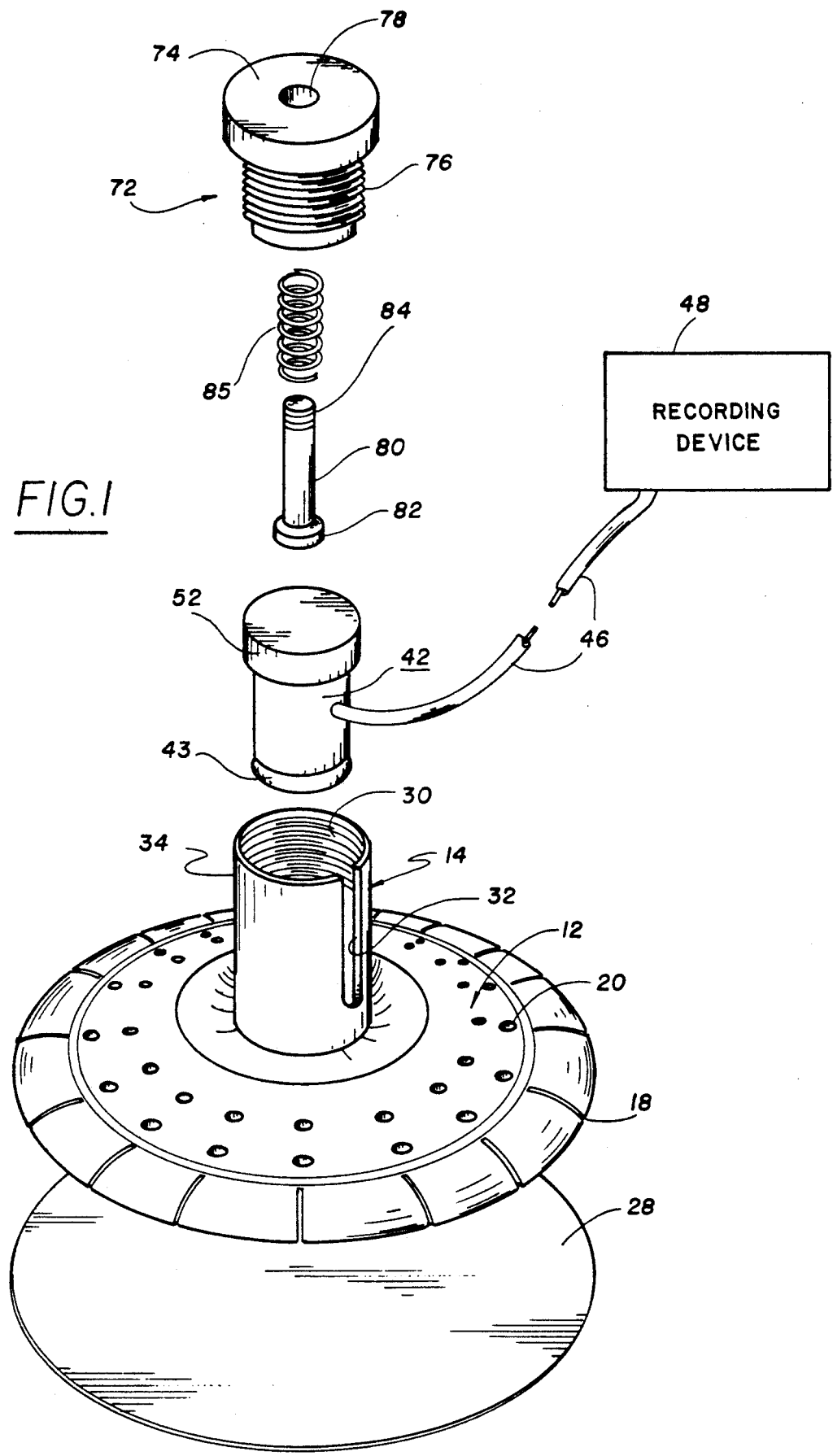

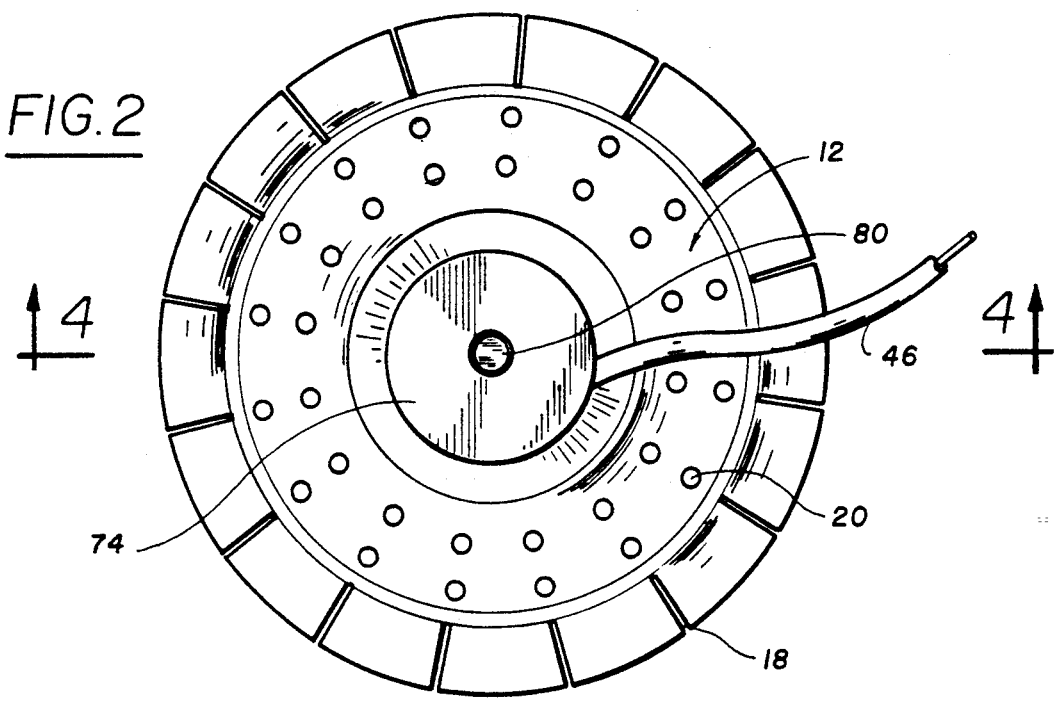
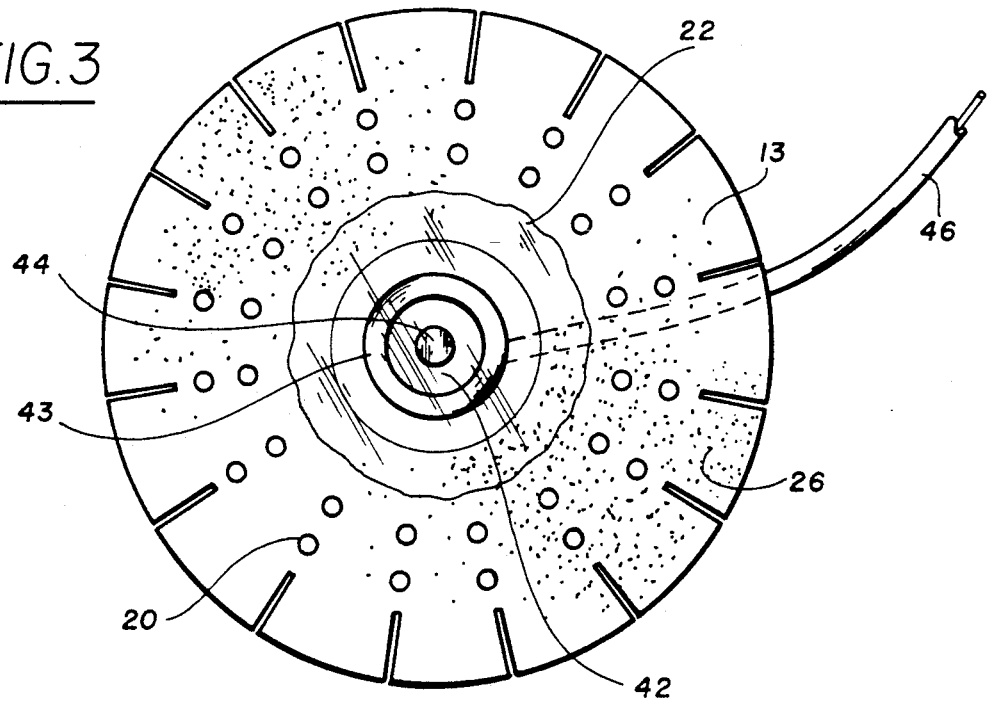

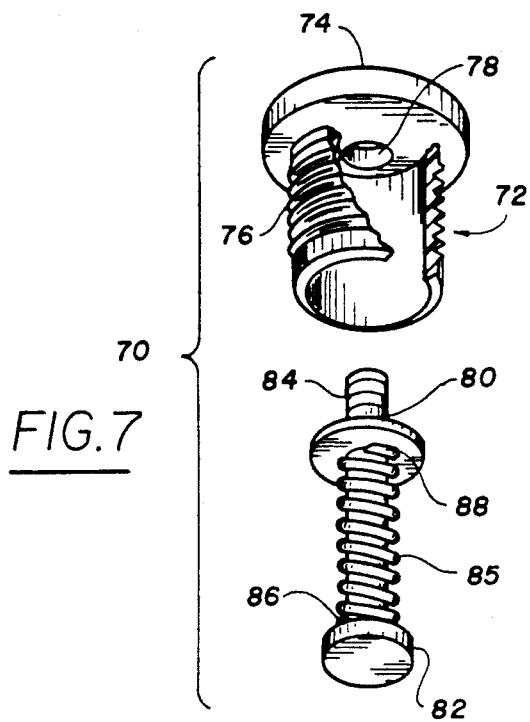
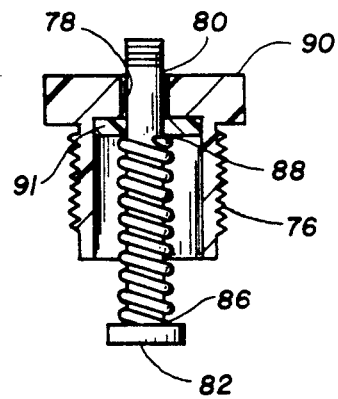
FIG.7
FIG.8
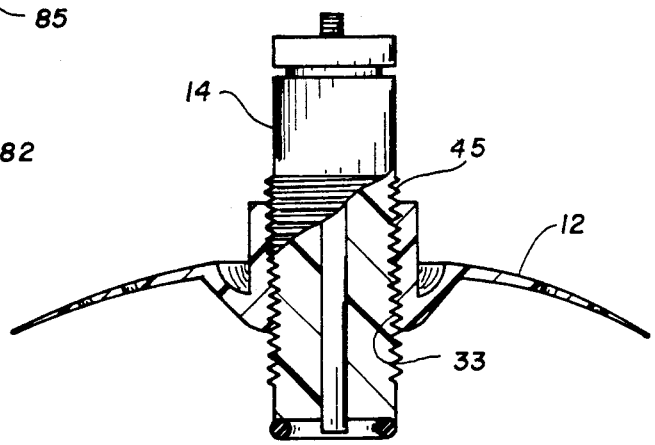
FIG.9A
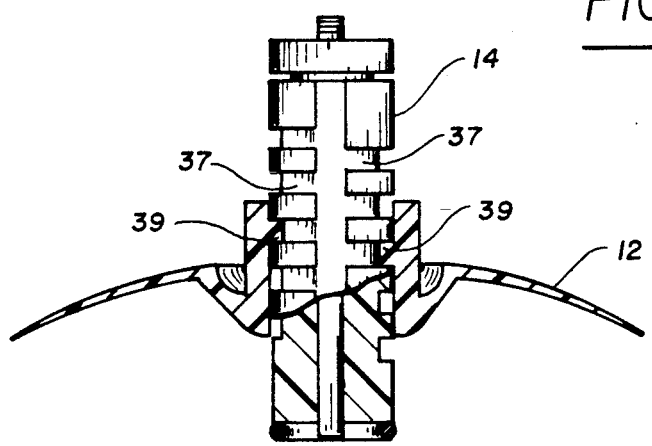
FIG.9B

EXTERNAL UTERINE CONTRACTION MONITORING DEVICE

RELATED APPLICATIONS

This is a continuation-in-part of patent application entitled CONTINUOUS CUTANEOUS BLOOD PRESSURE MEASURING APPARATUS AND METHOD, Ser. No. 780,398 filed by Edward H. Hon, M.D. and Edward D. Hon on Sept. 26, 1985, pending, and a continuation in part of patent application entitled Apparatus for Measuring Blood Pressure, Ser. No. 06/858,713 filed by Edward H. Hon, M.D. and Edward D. Hon on May 2, 1986, pending.

BACKGROUND OF THE INVENTION

The present invention relates to apparatus for monitoring uterine contractions during pregnancy and throughout labor and delivery. Information relating to the frequency, magnitude and pattern of such contractions is valuable to the physician, as a measure of the normal progression of labor. Additionally, it provides a guide for nurses and physicians in the use of medication or the need for other remedial actions.

The two types of apparatus most widely used at the present time for monitoring labor contractions are: (1) internal catheters inserted into the uterus to measure changes in the amniotic fluid pressure in the amniotic sac such as generally shown in the Pack U.S. Pat. No. 4,543,965; and (2) external devices which consists of a pressure transducer held in place on the abdomen of the patient by a belt fitted around the waist of the patient such as generally shown in the Fuzzell U.S. Pat. No. 3,520,294.

The most reliable device is the internal type. This means for measuring uterine contractions usually provides accurate data, but has a number of significant disadvantages which include:

1. The uterine cervix must be partially dilated and the amniotic sac ruptured.

2. During insertion of the catheter, bacterial and/or viral contaminants may be carried from the vagina and/or cervix into the uterine cavity and cause serious infection.

3. The catheter system may not be used where certain complications exist, e.g. uterine bleeding, here catheter insertion might cause additional bleeding; fever due to suspected uterine infection, in this case catheter insertion might exacerbate the situation.

4. If great care is not taken, during insertion of the catheter through its guiding tube, the lower segment of the uterus may be perforated.

5. Catheter insertion is uncomfortable for the patient and inconvenient and time consuming for the medical and nursing staff. Before insertion a sterile area must be prepared around the vaginal orifice and then draped with sterile towels. The catheter, catheter guide, fluid filled syringe and pressure measuring apparatus then have to be assembled. The entire operation usually takes 7-10 minutes.

6. Even though great care is exercised during catheter insertion, it is possible for the catheter to become clogged with a blood clot or vernix caseosa during labor so that the recorded uterine contraction data is compromised, sometimes to the point where it is not usable, even though the catheter system has been flushed with sterile water. In this case, the catheter must be replaced and the entire insertion process repeated.

7. During attempted flushing it is possible to damage the expensive pressure transducer if the flushing fluid is inadvertently directed towards the pressure transducer rather than towards the catheter.

8. Uterine contractions are often not monitored in the delivery room because current catheter systems usually place the pressure transducer directly on the fetal monitor so that patient transfer from labor to delivery room requires the reconnection of the catheter system to another pressure transducer on another fetal monitor---an awkward and time-consuming process. Additionally, it is difficult to maintain catheter sterility during the transfer process.

The external type of apparatus presently used consists of a pressure transducer held in place against the patient's abdomen by an encircling belt. The belt provides the counter-pressure which keeps the pressure transducer firmly against the maternal abdominal wall during contractions. Without it, the pressure transducer would merely ride up and down with each uterine contraction and hence would not reflect the changes in abdominal wall tension associated with uterine contractions.

While the external system is simple and convenient to use and does not suffer from some of the major disadvantages of the internal system, it too has significant problems, which include:

1. Even under the best of conditions the overall quality of data obtained by external means is not as precise as that obtained using an internal uterine catheter.

2. Uterine contraction data is easily compromised by fluctuations in belt tension. If the labor is intense and the patient moves, belt tension changes continually. Hence for satisfactory operation, the patient must be kept relatively immobile. Once belt tension has been altered by patient movement, the belt tension must be readjusted, otherwise no uterine activity data will be recovered.

3. When the patient is transferred from the labor ward to the delivery room the belt tension has to be readjusted. Because this can be time consuming, it is not usually done so that the external technique is infrequently used in the delivery room.

4. Because of the foregoing problems, current external uterine activity monitoring techniques provide at the best a fragmentary record of activity, even so, much of the data is of poor quality.

In the past, means other than a belt for fixing the external transducer to the patient's abdomen have been attempted.

As long ago as 1932 in "Surgery, Gynecology and Obstetrics," Vol. 55 (1932) at page 45, a tripod support assembly was disclosed which had an air transducer supported in a tripod-like structure which was fixed by tapes tied in ringlets of the tripod which was held fast by adhesive straps to the patient's loins. This structure was not widely employed and is not presently being used. In effect, this system conceptually was a precursor of the belt system.

Another prior art device disclosed in "Science-1947" at page 427 (shown diagramatically in FIG. 6) consisted of a heavy brass ring (240 grams) held in place on the abdomen by double coated Scotch brand adhesive tape applied to the bottom side. A strain gauge is held in the center of each ring by a single lever system. This system was devised by Dr. Reynolds, but has never been widely used and is not in use at the present time.

The Reynolds device used doubled-sided adhesive tape to prevent lateral movement of the rings. The weight of the rings provided counter-pressure to hold the strain gauge against the abdomen during episodic changes in abdominal wall tension which occurs with uterine contractions. Since the operation of the device depended on gravitational forces to hold the strain gauge in correct relationship to the abdominal wall, it was mandatory that the patient be on her back and be relatively immobile during the use of the device.

Because of the disadvantages of the external uterine contraction devices, the internal catheter system is considered the method of choice when accurate uterine contraction data is necessary for patient management.

OBJECTS OF THE PRESENT INVENTION

It is the object of the present invention to provide a continuous measurement of uterine contractions which is sufficiently accurate to provide a sound basis for patient management, yet at the same time not have the disadvantages inherent in an internal catheter system which have been cited previously.

It is a further object of this invention to provide a simple convenient method of more quickly attaching the device to the patient without causing patient discomfort.

It is a further object of this invention to provide a device that continually measures contractions more reliably than current existing external devices.

It is another object of the present invention to permit monitoring contractions without interfering with the patient's movement.

It is yet another object of the present invention to provide a monitoring device which is less expensive than existing contraction monitoring devices.

It is another object of the present invention to provide a monitoring apparatus which permits recording of uterine contraction activity at an earlier stage of pregnancy than existing contraction monitoring devices without inducing premature labor.

These and other objects of the present invention will be evident from the specification and accompanying drawings.

SUMMARY OF INVENTION AND OBJECTS

The present invention consists of an external device for measuring the frequency, magnitude and pattern of uterine contractions during labor. The device consists of a support base which is maintained in contact with the abdomen of the patient by adhesive and which is adapted to receive and hold a removable sensor against the abdomen of the patient.

The support base is concave for adapting to the shape of the abdomen. A cylindrical hollow tube projects through the center of the support base to support a housing for a sensor, which is typically a pressure transducer, which is held firmly against the abdomen of the patient. Other sensing devices can also be used, such as are known in the art. The tube may be integrally formed with the base or removably attached to the base. The signal output of the transducer is connected by wires to a conventional amplifying and recording means.

The pressure transducer is fixed in a housing which is removably affixed within the hollow tubular member of the support base so that the transducer and its housing can be separated from the support base and the support base discarded after use thereby permitting a sterile support base to be brought into contact with the patient's skin with each use. A flexible membrane is fitted across the opening of the hollow tube so that the active surface of the transducer does not actually come into contact with the abdomen thereby maintaining the transducer in a clean condition and at the same time preventing contamination of the sensor by the glue and other preparatory material used in maintaining the support base on the abdomen.

The support base has a series of small openings through its entire thickness so that a glue dissolving chemical may be disbursed through the openings onto the skin, permitting easy removability of the support base from the abdomen wall.

In the preferred embodiment an isolation ring surrounds the active surface of the transducer thereby isolating and confining a portion of the abdominal wall tissue. The transducer measures the pressure changes in this confined portion of tissue which, because of its relative isolation from the other parts of the maternal abdominal wall tissue, is less subject to patient movement. As a result, this device permits more accurate measurements of uterine contractions than available with prior existing external contraction sensing devices.

Further details of the invention will be evident from a review of the following descriptions of the drawings and the detailed description of the invention.

BRIEF DESCRIPTION OF THE DRAWINGS

FIG. 1 is an exploded perspective view of the monitoring apparatus.

FIG. 2 is a top view of the monitoring apparatus.

FIG. 3 is a bottom view of the monitoring apparatus of FIG. 2.

FIG. 7 is a partial exploded view of the pressure adjusting assembly.

FIG. 8 is a sectional view of the assembled pressure adjusting assembly.

FIGS. 9a and 9b are side-sectional views of a height adjusting means of the tubular member.

DETAILED DESCRIPTION OF THE INVENTION

Figure 4:
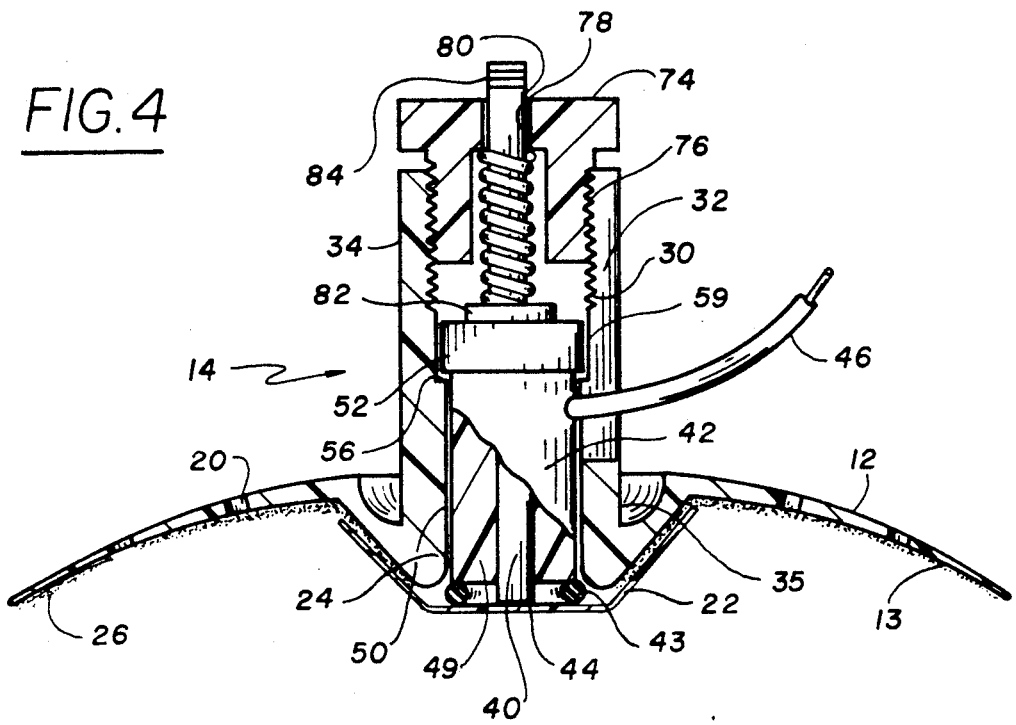
FIG. 4 is a side-sectional view of the monitoring apparatus of FIG. 1 taken along lines 4-4 of FIG. 2.
Figure 6:
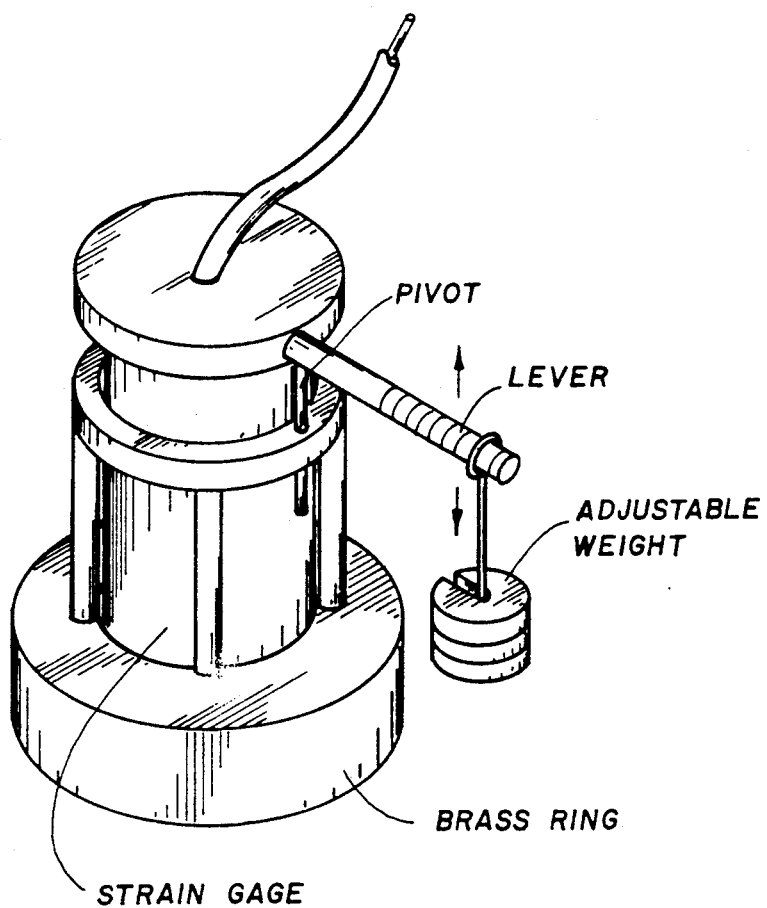
FIG. 6 is a representation of a 1947 prior art external device which does not use a belt.

Making reference to FIGS. 1 through 4, a concave support base 12 has a hollow tubular fitting 14 mounted perpendicular substantially at the center of the support base 12 projecting above and below the support base 12. The hollow tubular fitting 14 may be formed integrally with the support base 12 or removably fixed to the support base 12 by threads, force fitted or other coupling means.

The tubular fitting has an internal diameter of approximately 1 inch. The upper portion 34 of the hollow tubular fitting 14 extends approximately 1½ inches above the support base 12 and the lower portion 35 of the tubular fitting 14 extends below the support base approximately ½ inch.

The support base 12 is slightly thicker near its center, gradually tapering out to a thinner thickness at its edges and around the perimeter of the support base 12 making the support base somewhat flexible so as to permit the support base 12 to more readily conform to the shape of the abdomen of a pregnant patient. A series of radial scores or slots 18 are formed around the circumference of the support base 12 to further assist in the flexibility of the support base 12. In the preferred embodiment of the invention the thickness of the support base at its center is approximately ⅛ inch and at its edges is approximately 1/10 inch. The diameter of the support base 12 is approximately 4 inches. A plurality of small openings 20 pass through the support base 12.

In one embodiment of the invention, the entire support base is formed from a relatively flexible rubber-like material, thereby more readily adapting to the contour of the patient. Slots or scoring could still be employed with this embodiment.

The depth of the lower portion 35 is a function of the firmness of the abdomen of the patient. In most applications a depth of ¼ inch is sufficient. However, in the case of extremely obese patients a depth of ¾ inch or even 1 inch may be desirable.

In one embodiment the tubular member 14 is not formed integrally with the support base 12. In such an embodiment the depth of the tubular member extending below the bottom surface 13 of the support base 12 may be varied by having an external screw thread 45 on the tubular member engaging internal thread 33 on the support base 12, permitting its position to be varied, as shown in FIG. 9a. Use of slip notches 37 cooperative with notches 39, such as shown in FIG. 9b, may also be employed.

A flexible protective membrane 22 is fixed so as to surround the entire circumference of the lower end 24 of the hollow tubular fitting 14 by glue or heat sealing, thereby forming a sterile and waterproof seal around the opening in the lower end of the hollow tube fitting 14.

An alcohol soluble adhesive layer 26 extends over the bottom surface 13 of the support base 12. The adhesive layer 26 is a conventional medical adhesive which is not likely to cause a reaction with the skin of the patient. Fitted over the glue layer and over the flexible protective membrane 22 is a removable backing sheet 28.

A portion of the interior of the hollow tubular fitting 14 is thread 30 and a slot 32 is located in the wall of the upper portion 34 of the tubular fitting 14. The interior of hollow tubular fitting 14 has a decreased diameter portion 50 forming a shoulder 56 for receiving a transducer assembly 42 having an increased diameter portion 59.

The transducer assembly 42 includes a transducer 40 which is a conventional, commercially available transducer such as sold by Transamerica Delaval Inc. which measures pressure applied to its active surface 44. Electrical lead wire 46 from the transducer 42 provides an electrical output signal response to the pressure applied to the active surface 44, is connected to a conventional strip chart recorder shown diagramatically as 48. The transducer 40 forms an integral unit 42 with a surrounding retaining structure 49.

Referring to FIGS. 7 and 8, the pressure adjusting assembly 70 is shown as comprising a cylindrical member 72 having an external thread 76 around its circumference corresponding to the internal thread 30 of hollow tubular fitting 14. The cap 74 of the cylindrical member 72 has a larger diameter and a circular opening 78. Cylindrical pressure indicating rod 80 has an outer diameter slightly smaller than the diameter of the opening 78 and an increased diameter portion 82 at its lower end. Parallel spaced scribe marks 84 which may be of different colors are located at its upper end. A helical spring 85 is attached at one of its ends 86 to a point above and proximate the increased diameter portion 82 of the pressure indicator 80 and at its other end 88 to a washer 91 fitted fixedly within the interior of the cylindrical member 74 of the pressure adjusting assembly 70. The pressure indicating rod 80, with the spring in the uncompressed position, extends only slightly above the top surface 90 of the cap 74.

In assembly, the transducer assembly 42 within the cylindrical hollow tubular fitting 14 with the wire 46 passing through the slot 32 in the side wall of the hollow tubular fitting 14. Shoulder 52 of the retaining structure 48 fits above shoulder 56.

The pressure adjusting assembly 70 is then fitted within the cylindrical hollow tube 14. The pressure adjusting assembly 70 has its external thread 76 engaged in the internal threads 30 of the hollow tubular fitting 14. The pressure adjusting assembly is turned until the pressure on the transducer from the spring 85 is achieved as indicated by the scribe marks 84 on the top end of the pressure indicating rod 80.

Surrounding the active end 44 of the transducer 42 and projecting slightly below the active surface 44 is an isolation ring 43 which serves to accentuate and stabilize the transference of internal pressure, isolating the surface area from extraneous vibrations.

In operation of the apparatus the abdomen of the patient is first cleansed by a sterile alcohol preparation. Then an adhesive binder solution is applied to the abdomen. Such adhesive binders assure good contact with the adhesive layer 26 which is on the lower surface 13 of the support base 12. Typical adhesive binders are sold under the trademark SKIN SHIELD and are known as liquid bandages. The adhesive binder is alcohol soluble.

The backing sheet 28 is then removed from the adhesive layer 26 on the support base 12. An example of the adhesive layer and backing is commercially available as a product from 3M Company sold under the trademark STOMASEAL. The support base 12 has its inner bottom surface 13 pressed against the abdomen distending the slots 18 and slightly deforming the support base 12 so that the support base 12 conforms substantially to the shape of the abdomen of the patient. The support base 12 is momentarily held in place to assure adequate drying and good contact.

While the support base 12 is provided with its own adhesive layer, it is possible to apply an adhesive directly to the patient's abdomen. Obviously, the control of the adhesive is not as great as in the preferred embodiment.

The transducer assembly 42 is then fitted within the hollow tubular fitting 14 so that the active face of the transducer 44 and the isolation ring 43 is in contact with the flexible membrane 22 which is pressed against the abdomen. The lead wire 46 is then connected to the recording device 48 and the member 72 is then put in place and tuned, compressing the spring 85 and causing the element 82 to press against the transducer assembly 42 and accordingly causing the isolation ring 43 and the active element 44 of the transducer to be pressed against the abdomen of the patient through the membrane 22.

The amount of pressure applied to the abdomen may be determined by the position of the score marks 84 projecting above the top surface 90 of the cap member 74. Different colored segments may be used in place of or in association with the score marks.

The pattern of the contractions may now be observed on the recording apparatus. The transducer assembly can be removed from the support base 12 at any time, leaving the support base 12 in place. Thus, the patient can be moved from one location to another by disconnecting the lead wire 46 from the recorder or by removing the transducer assembly 42. The base plate 12 remains in place since the adhesive is sufficiently strong to form a fixed base relative to the skin of the patient.

Additionally, the patient can stand or move around with the monitoring apparatus in place, something that cannot be done with the prior art monitoring devices unless the encircling belt tension is frequently readjusted.

The adhesive bond formed between the abdomen and the support base is sufficiently strong to prevent the lifting of the support base 12 when subjected to the downward pressure of the transducer assembly 42. Further, the monitoring apparatus can be used, without adjusting the base line of the recording apparatus, whether the patient is lying down or standing up.

Figure 10:
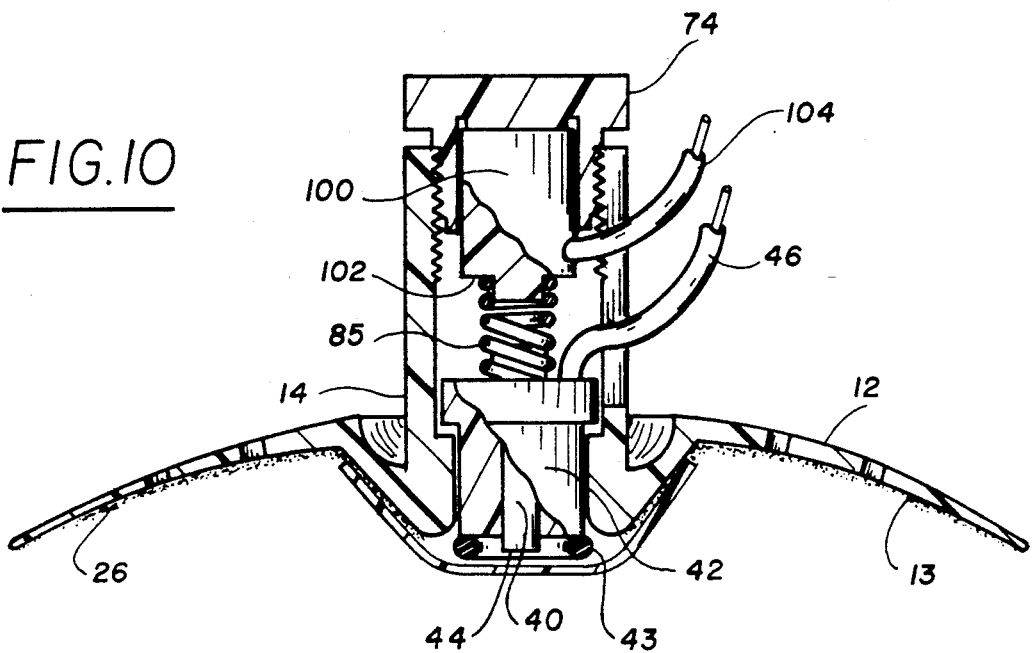
FIG. 10 is an alternative embodiment of the monitoring device having a second sensor for adjusting the pressure.
Figure 11:
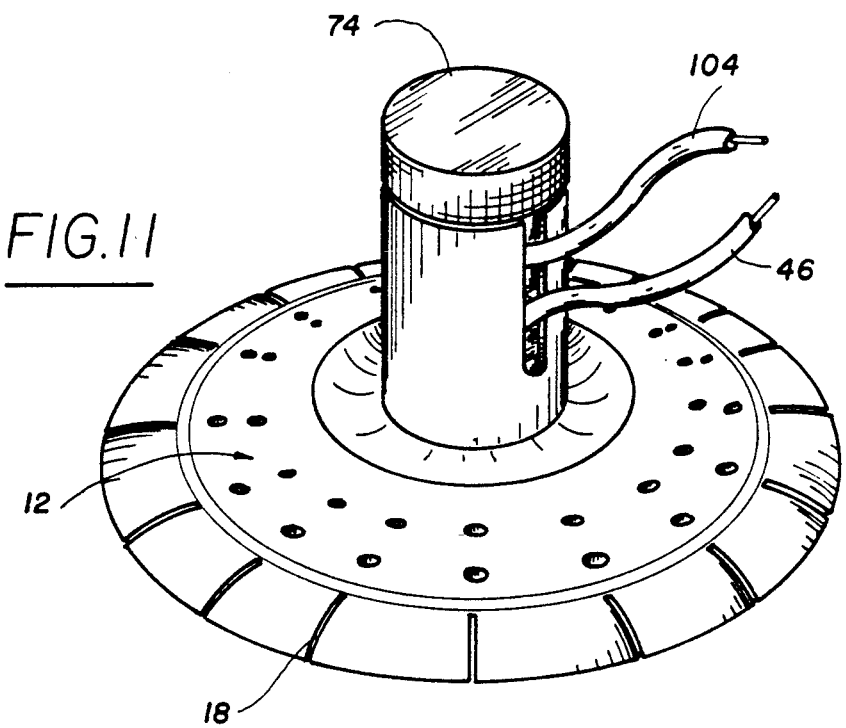
FIG. 11 is a top perspective view of the monitoring apparatus of FIG. 10.

Referring to FIGS. 10 and 11, an alternative embodiment of the invention is shown in which there is a modified apparatus for adjusting the pressure applied to the transducer assembly 42. A second transducer assembly 100 is mounted above spring 85 so that the active surface 102 of the second transducer assembly 100 measures the pressure applied to the abdomen can be determined.

Once the monitoring apparatus has completed its purpose, the transducer assembly is removed and an adhesive solvent is applied through the openings 20 to the bottom surface 13 of the support base 12 so that the solvent dissolves the adhesive 26 holding the support base 12 in place. The support base may then be readily removed from the patient with minimal discomfort.

The support base 12 may then be disposed of and a new support base, which is maintained in a sterile container, having a fresh flexible membrane, for future use.

Figure 5A:
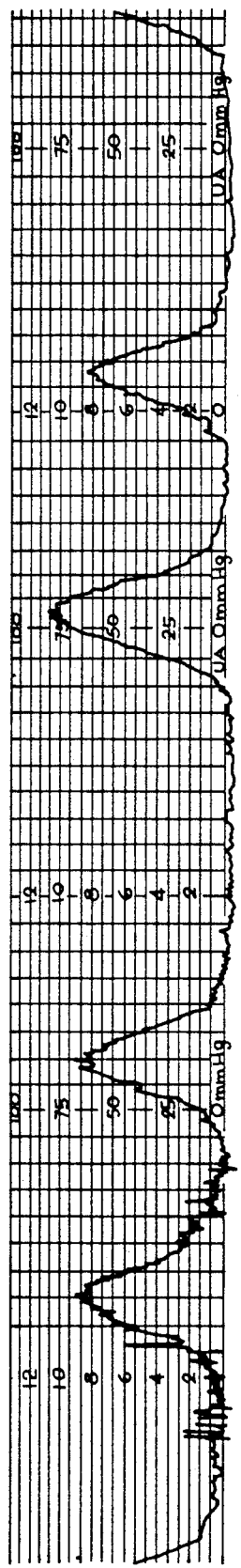
FIG. 5a is the contraction pattern obtained by use of the prior art internal catheter monitoring device.
Figure 5B:
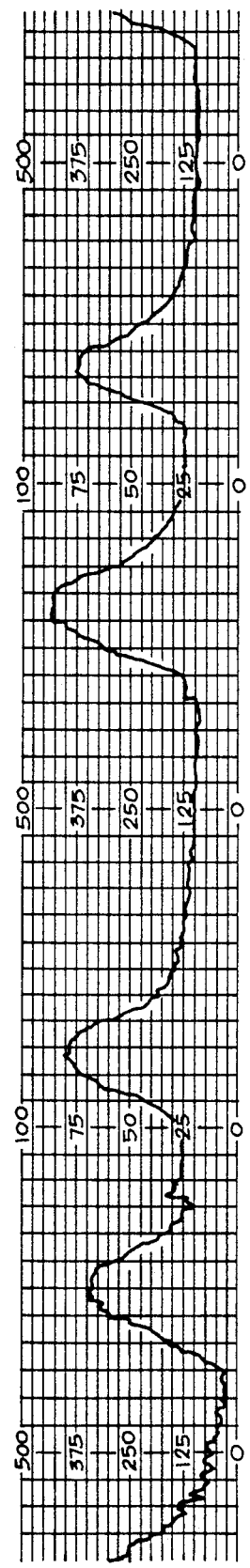
FIG. 5b is the contraction pattern obtained using the monitor of the present invention.
Figure 5C:
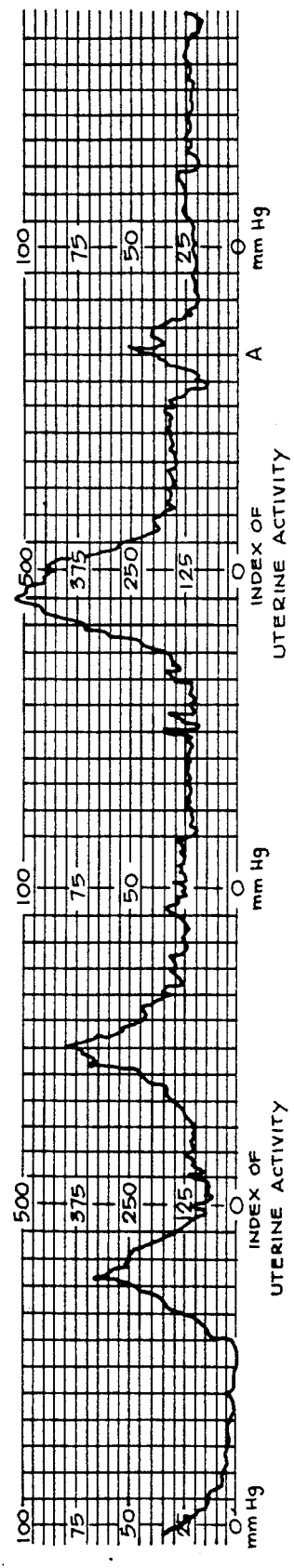
FIG. 5c is the contraction pattern of the prior art external monitoring device.

Referring to FIGS. 5a-5c, the comparisons between the data obtained from the existing prior art devices, both internal and external, are shown.

FIG. 5a is a record of four (4) uterine contractions made with an internal system where a small diameter plastic tube has been inserted into the uterus. This invasive system provides the most precise data currently available. Uterine contraction amplitudes and durations are measured accurately unless the plastic tube becomes partially or completely occluded.

FIG. 5b is a record made simultaneously with the external device which is the subject of this invention. Note the marked similarity between both these records, both from the standpoint of relative amplitude and duration.

FIG. 5c is another record made simultaneously with a currently used external uterine contraction device. Comparison of each contraction (proceeding from left to right) with the two previous records (FIGS. 5a and 5b) show their marked differences. This is especially true of the fourth contraction in FIG. 5c (marked with an A).

Because of the close similarity of the records obtainable with the external device which is the subject of this invention and the records obtained with the invasive internal system, the external device could replace the internal system in the majority of cases.

It is recognized that variations in the invention can be made without departing from the concept of the present invention of which:

What I claim is:

1. Apparatus for monitoring labor contraction comprising,
    (a) a relatively rigid plate like support base capable of conforming to the abdomen of a patient, and adapted to be relatively fixed to the abdomen of a patient by adhesive means said support base having an upper surface and a lower surface, said lower surface having an adhesive layer; and
    (b) said support base having holding means for holding a removable pressure transducer sensing means against the abdomen.

2. The apparatus of claim 1 in which said support base is concave so as to conform to the shape of the abdomen.

3. The apparatus of claim 2 in which said support base is capable of distorting so as to conform to the shape of the abdomen.

4. The apparatus of claim 1 in which said support base has score means associated therewith for increasing the flexibility of at least a portion of the support base.

5. The apparatus of claim 4 in which said score means are centrally configured.

6. The apparatus of claim 1 in which said support base has a plurality of openings therethrough.

7. The apparatus of claim 1 in which said holding means comprises an opening in said support base.

8. The apparatus of claim 1 in which said holding means comprises a hollow tubular member forming an opening in said support base.

9. The apparatus of claim 8 including a flexible membrane fitted across said opening in said support base.

10. The apparatus of claim 8 in which said hollow tubular member is formed integral with said support base.

11. The apparatus of claim 8 in which the said hollow tubular member is removably fixed to said support base.

12. The apparatus of claim 11 in which said hollow tubular member has a portion extending below the lower surface of said support base.

13. The apparatus of claim 11 in which the hollow tubular member is adjustable in relation to said support base.

14. Apparatus for monitoring contractions comprising a concave support base capable of deforming so as to conform to the shape of the patient having an upper surface and a lower surface adapted to conform to the shape of the abdomen of a patient;
    an adhesive layer attached to said lower surface of said support base;
    said support base having a hollow tubular holding member passing through said support base forming an opening fixed substantially perpendicular to the support base and passing through said support base;
    said hollow tubular member being adapted to hold a pressure transducer sensing means.

15. The apparatus of claim 14 in which a flexible membrane member is fitted across said opening proximate said lower surface of said support base.

16. The apparatus of claim 14 including scored portions on said support base.

17. Apparatus for monitoring labor contractions comprising:
   (a) a support base comprising a thin relatively rigid plate-like member having an upper and a lower surface, said support base shaped so as to conform to the shape of an abdomen of a patient;
   (b) means associated with said support base for holding a pressure transducer sensing means against the abdomen of a patient; and
   (c) adhesive means associated with said lower surface of said support base for holding the support base relatively fixed to the abdomen so as to prevent movement of said support base against lateral or vertical movement.

18. The apparatus of claim 17 in which said support base is concave.

19. The apparatus of claim 17 in which a flexible membrane is attached to the lower surface of said support base for preventing said pressure transducer sensing means from coming into contact with the patient.

20. Apparatus for monitoring contractions comprising:
   (a) a support base capable of conforming to the abdomen of a patient having an opening therein and an upper and lower surface adapted to be adhesively held against the abdomen of a patient, said support base having an upper and a lower surface and an adhesive layer on its lower surface sufficiently strong so that it will withstand substantial lateral and vertical force against the support base when attached to the abdomen of a patient; and
   (b) a first pressure transducer sensing means removable associated with said support base, said first sensing means having an active surface and passing through said support base for having the active surface pressed against the abdomen of a patient.

21. The apparatus of claim 20 in which said support base is concave.

22. The apparatus of claim 20 wherein said support base is capable of distorting so as to conform to the shape of the abdomen when pressed there against.

23. The apparatus of claim 20 in which said first transducer sensing means is removably fixed to said support base.

24. The apparatus of claim 20 in which said first transducer sensing means is held fixed to said support base in a hollow tubular member passing through said support base.

25. The apparatus of claim 24 in which said hollow tubular member extends below the lower surface of said support base.

26. The apparatus of claim 24 in which a flexible membrane is attached to the lower surface of said support base covering the opening of said hollow tubular member.

27. The apparatus of claim 20 in which there are a plurality of openings passing through said support base.

28. The apparatus of claim 20 in which at least a portion of said support base is flexible.

29. The apparatus of claim 20 in which said support base includes a plurality of holes therethrough.

30. The apparatus of claim 20 in which said support base has weakened portions for making portions of said support base flexible.

31. The apparatus of claim 30 in which said support base is disc shaped and said weakened portion comprises a plurality of radial scores.

32. The apparatus of claim 31 in which said weakened portion comprises at least one score adjacent the circumference of said support base.

33. The apparatus of claim 20 additionally comprising a pressure adjusting assembly which can hold said first pressure transducer against the abdomen with varying degrees of pressure.

34. Apparatus for monitoring labor contractions comprising:
   (a) a support base having an opening therein and an upper and lower surface adapted to be adhesively held against the abdomen of a patient, said support base having an upper and a lower surface and an adhesive layer on its lower surface sufficiently strong so that it will withstand substantial lateral and vertical force against the support base when attached to the abdomen of a patient; and
   (b) a first pressure transducer sensing means removably associated with said support base, said first sensing means having an active surface and passing through said support base for having the active surface pressed against the abdomen of a patient in which said first transducer sensing means includes an isolating means associated with said active surface.

35. The apparatus of claim 34 in which said isolating means comprises a ring-like member surrounding the active surface of said first transducer sensing means.

36. The apparatus of claim 34 in which said isolating means comprises a ring surrounding the active surface of the pressure transducer and extending below said active surface.

37. The apparatus of claim 36 in which the diameter of said active surface is substantially smaller than the inner diameter of said ring.

38. The apparatus of claim 37 in which the diameter of said active surface is less than one half the inner diameter of said ring.

39. The apparatus of claim 34 in which said isolating means is the hollow tubular member.

40. Apparatus for monitoring contractions comprising:
   (a) a support base having an opening therein and an upper and lower surface adapted to be adhesively held against the abdomen of a patient, said support base having an upper and a lower surface and an adhesive layer on its lower surface sufficiently strong so that it will withstand substantial lateral and vertical force against the support base when attached to the abdomen of a patient; and
   (b) a first pressure transducer sensing means removable associated with said support base, said first sensing means having an active surface and passing through said support base for having the active surface pressed against the abdomen of a patient in which said first transducer first pressure sensing means includes visual means for determining the initial pressure applied to said first pressure first transducer sensing means; and
   (c) a pressure adjusting assembly which can hold said first pressure transducer against the abdomen with varying degrees of pressure, said assembly including visual means for indicating the pressure applied to said first pressure transducer by said assembly.

41. The apparatus of claim 40 in which said visual means comprises a projecting member having markings thereon, said projecting member held in contact with said first pressure first transducer sensing means by a spring means, the markings being indicative of the pressure of the spring means against the first transducer sensing means.

42. Apparatus for monitoring contractions comprising:
(a) a support base having an opening therein and an upper and lower surface adapted to be adhesively held against the abdomen of a patient, said support base having an upper and a lower surface and an adhesive layer on its lower surface sufficiently strong so that it will withstand substantial lateral and vertical force against the support base when attached to the abdomen of a patient; and
(b) a first pressure transducer sensing means removable associated with said support base, said first sensing means having an active surface and passing through said support base for having the active surface pressed against the abdomen of a patient in which a second transducer pressure sensing means senses the position of said first transducer sensing means; and
(c) a pressure adjusting assembly which can hold said first pressure transducer against the abdomen with varying degrees of pressure, said assembly including a second transducer pressure sensing means to sense the pressure applied to said first pressure transducer by said assembly.

43. The apparatus of claim 42 in which said first and second pressure transducers have outputs connectable to a monitoring device, the apparatus additionally including switching means for switching the output form the first and second transducer pressure sensing means to the monitoring device.

44. Apparatus for monitoring contractions comprising a relatively flexible support base, said support base having an upper surface and a lower surface, said support base being adapted to conform to the shape of the abdomen of a pregnant patient, said support base having an opening therein for receiving a transducer pressure sensing means, and a flexible membrane attached to the lower surface of said support base covering said opening.

45. The apparatus of claim 44 in which said support base is substantially circular and has an outer diameter of approximately four times the diameter of said opening in said support base.

46. The apparatus of claim 45 in which said support base has an adhesive layer on the lower surface.

47. The apparatus of claim 44 in which said support base has a hollow tubular member associating with the opening to receive the transducer pressure sensing means.

48. A transducer sensing means assembly comprising a first pressure transducer sensing means for sensing displacement; said first pressure transducer sensing means having an active surface on one end thereof and a non-active surface on a second end; and an indicating means for indicating the pressure applied to the non-active end of said pressure transducer sensing means.

49. The apparatus of claim 48 in which said indicating means includes visual means for determining the initial pressure applied to said first pressure transducer sensing means.

50. The apparatus of claim 49 in which said visual means comprises a projecting member having markings thereon, said projecting member held in contact with said first pressure transducer sensing means by a spring means, the markings being indicative of the pressure of the spring means against the first pressure sensing means.

51. The apparatus of claim 48 in which a second pressure transducer sensing means senses the pressure applied to the non-active surface of said first transducer sensing means.

52. The apparatus of claim 51 in which said first and second pressure transducers have outputs connectable to a monitoring device, the apparatus additionally comprising switching means for switching the output from the first and second pressure transducers to the monitoring device.

53. Apparatus for monitoring labor contractions comprising;
(a) a relatively rigid support base adapted to be relatively fixed to the abdomen of a patient by adhesive means, said support base having a normally concave shape so as to conform to the shape of the abdomen and an opening therethrough for the passage of a pressure transducer means; and
(b) Means for holding a pressure transducer means against the abdomen of the patient.

54. The apparatus of claim 53 in which said support base has an inner portion proximate said opening relatively rigid in relationship to the outer portion.

55. The apparatus of claim 54 in which said support base is tapered from a thicker portion proximate the center of the support base to a thinner portion along the periphery of the support base.

56. The apparatus of claim 53 in which the support base has an upper surface and a lower surface, said lower surface having a double-sided adhesive means applied thereto.

57. The apparatus of claim 56 in which said lower surface has a flexible membrane surrounding the central opening.

58. A pressure transducer assembly comprising,
(a) a first pressure transducer having an active surface on one end thereof and a non-active surface on the other end thereof; and
(b) a second pressure transducer having an active surface on one end thereof, said active surface of said second pressure transducer being in contact with the non-active end of said first pressure transducer.

59. The pressure transducer assembly of claim 58 in which said first pressure transducer and said second transducer are aligned along the same axis.

60. The pressure transducer assembly of claim 58 in which said first pressure transducer and said second transducer have electrical outputs connectable to a monitoring device.

61. The pressure transducer assembly of claim 60 including switching means for switching the output from said first and second pressure transducers to the monitoring device.

62. The pressure transducer assembly of claim 59 in which said pressure transducers are mounted in a single housing.

63. A method for monitoring the labor contractions of a patient comprising the steps of:

a. adhesively applying a relatively rigid support plate like member having a holding means for holding a pressure transducer to the abdomen of the patient;

b. inserting the pressure transducer into the holding means whereby the active surface of the pressure transducer is pressed against the abdomen of the patient; and c. recording the output of the pressure transducer caused by the contractions.

64. The method of claim 63 in which said pressure transducer includes an isolation means surrounding the active surface of said pressure transducer.

65. The method of claim 63 in which said holding means comprises a hollow tubular member for firmly holding said pressure transducer in a fixed position relative to said support plate.

* * * * *